United States Patent
Davidner et al.

(10) Patent No.: US 6,193,681 B1
(45) Date of Patent: Feb. 27, 2001

(54) SEPTICEMIA PREVENTION AND TREATMENT SYSTEM

(75) Inventors: Alan Davidner, Claremont; H. Vernon Roohk, Westminster, both of CA (US); Richard G. L. Chan, Oyster Bay, NY (US)

(73) Assignee: American Immuno Tech, LLC., Costa Mesa, CA (US)

( * ) Notice: Subject to any disclaimer, the term of this patent is extended or adjusted under 35 U.S.C. 154(b) by 0 days.

(21) Appl. No.: 09/152,528

(22) Filed: Sep. 14, 1998

(51) Int. Cl.[7] .................................................. A61L 2/00
(52) U.S. Cl. .................... 604/6.08; 604/4.01; 604/5.01; 422/24; 205/432 R; 205/435; 205/437; 607/88; 607/90; 607/94
(58) Field of Search .................. 128/DIG. 3; 422/44–48, 422/22, 24; 604/4.01, 6.08, 5.01–6.05, 6.09, 6.1, 6.11, 6.14, 6.16; 250/428, 430, 432 R, 438, 434–36, 503.1, 504 R; 607/88, 90–94

(56) References Cited

U.S. PATENT DOCUMENTS

| | | | |
|---|---|---|---|
| 4,559,034 | * | 12/1985 | Kirita et al. ............................ 604/52 |
| 4,683,889 | * | 8/1987 | Edelson ................................ 128/395 |
| 4,708,715 | * | 11/1987 | Troutner et al. ......................... 604/6 |
| 4,737,140 | * | 4/1988 | Lee et al. ................................. 604/4 |
| 5,288,605 | * | 2/1994 | Lin et al. ............................. 435/902 |
| 5,433,738 | * | 7/1995 | Stinson ................................. 607/92 |
| 5,459,030 | * | 10/1995 | Lin et al. ................................. 435/2 |
| 5,496,637 | * | 3/1996 | Parham et al. ....................... 428/376 |
| 5,730,713 | * | 3/1998 | Okarma et al. ........................... 604/6 |
| 5,951,509 | * | 9/1999 | Morris ................................... 604/4 |
| 6,042,783 | * | 3/2000 | Nagamatsu et al. .................. 422/44 |

* cited by examiner

Primary Examiner—Angela D. Sykes
Assistant Examiner—Patricia Bianco
(74) Attorney, Agent, or Firm—G. Donald Weber, Jr.

(57) ABSTRACT

A method and apparatus for preventing and treating septicemia in patient blood. The extracorporeal system includes an anti-microbial device to kill at least 99% of bloodborne microorganisms, a hemoconcentrator/filtration unit to remove approximately 90% of target molecules from the patient blood and a filter unit to remove target molecules from patient blood from the sieved plasma filtrate. Target molecules are produced by microorganisms as well as the patient's cells and include endotoxins from gram negative bacteria, exotoxins from gram negative and gram positive bacteria, as well as RAP protein mediator from *Staphylococcus aureus*, and cell mediators such as tumor necrosis factor-alpha, and interleukin 1-beta, complement proteins C3a and C5a, and brandykinin.

30 Claims, 5 Drawing Sheets

SEPTICEMIA PREVENTION AND TREATMENT SYSTEM

BACKGROUND

1. Field of the Invention

The present invention relates, generally, to methods of and apparatus for killing bloodborne microorganisms by ultraviolet irradiation and removing target molecules from the blood by a hemoconcentrator/filter and, subsequently, removing some target molecules from the ultrafiltrate by additional filtration for endotoxins and cell mediators before returning to the blood.

2. Prior Art

Septicemia refers to a microbe-induced condition in which the patient experiences an exaggerated inflammatory response. This response can lead to varying degrees of hypotension (possibly shock), and hypoxemic and edema-related organ failure called multiple organ dysfunction syndrome (MODS). Because trauma and burns, among other causes, can lead to MODS, in the absence of infection, the more current and generic term is systemic inflammatory response syndrome (SIRS).

Between 1980 and 1992 the death rate due to septicemia increased 83% from 4.2 to 7.7 per 100,000 population. The greatest increases were seen in patients at least 65 years old. Bacterial infections accounted for approximately 200,000–300,000 cases of septicemia as of 1992, and was the 13th leading cause of death nationally. The mortality rate averaged 35%, with a range of 20–65%, and accounted for approximately 100,000 deaths.

Septicemia is usually categorized by the particular group of microorganism involved, i.e., bacterial, gram negative or gram positive, and fungal. Gram negative bacteria of concern include *Pseudomonas aeruginosa, Eschericia coli,* and *Enterobacter aerogenes*. Gram positive bacteria of interest include *Staphylococcus aureus, Streptococcus pneumoniae,* and Enterococcus spp. The usual fungus involved is the yeast, Candida spp. Septicemia and related conditions develop when certain microorganisms, the cellular products, and other target molecules stimulate cascade reaction and an exaggerated inflammatory response leading to multiple organ and system failure. Selected microbial products and other target molecules, with molecular weights, are shown in Table 1.

TABLE 1

Selected Target Molecules of Concern in Septicemia and Potentially Removed by SPATS

| Molecule | Molecular Weight - KiloDaltons (kD) |
| --- | --- |
| Endotoxins (gram negative bacteria) | 10–40 |
| Tumor Necrosis Factor, alpha(TNF-a) | 17–51 |
| Interleukin 1, beta(IL 1-p) | 17 |
| Exotoxins (gram positive and gram negative bacteria) | |
| gram+ (Diphtheria) | 65 |
| gram− (Cholera) | 82 |
| RAP, protein (*Staphylococcus aureus*) | 50 |
| Complement 3a and 5a | 9–11 |
| Bradykinin | 1 |

These target molecules may enhance the microbe's virulence and/or stimulate the patient's defense mechanisms, but, when excessive, they may lead to multiple organ system failure. These microorganisms, their cellular products and the target molecules can stimulate various cascade reactions which may result in a life-threatening inflammatory disease state.

Prevention of these medical conditions is difficult at best because the early signs and symptoms may be quite vague. Treatment has generally been instituted when the condition is recognized which is, unfortunately, often very late in the course of the disease. With prophylaxis difficult and therapy often late, the results may be fatal for the patients in many cases. Treatment of the early viremic stage of H.I.V. on the other hand, is possible. The signs and symptoms are recognizable by a trained physician and reduction of the viral load has been shown to improve the prognosis of the disease. This reduction in viral load may also be effective at later stages of H.I.V. infections. We believe that the ability of SPATS to reduce bacterial load, as well, by 99% or more will also serve a significant role in the prevention of septicemia in patients undergoing coronary bypass, dialysis, and probably other conditions. SPATS can also be used to treat septicemia in patients undergoing such invasive procedures.

Ultraviolet blood irradiation (UBI)—originally the Knott technique—has been used in the United States since 1928 for the successful extracorporeal treatment of microbial infections. Over the years there have been scientific arguments concerning the mechanism by which UBI works and the consensus appears to be that some organisms are killed and a stimulated immune system then protects the patient by clearing the remaining organisms from the body.

Hemoconcentrator/filtration units are used to remove water from patients who are in acute renal failure and become overly hydrated. The devices are designed to retain all plasma proteins, including the smallest albumin, (molecular weight of 67–69 kD), while ridding the blood of excess water. Current membranes and/or hollow fiber systems have effective pore sizes which will pass molecules up to 30–50 kD.

The Lee et al patent describes the removal of the "toxic mediators" of SIRS by the continuous arteriovenous hemofiltration of whole blood by processing with a filter having a pore size adequate to remove substances up to 100–150 kD (although the probable size of the molecules removed is 10–40% less due to occlusion of the pores by plasma proteins).

PRIOR ART STATEMENT
U.S. Patents

| | | |
| --- | --- | --- |
| 5,571,418 | 11/1996 | Lee et al. |
| 5,211,850 | 5/1993 | Shettigar et al |
| 5,211,849 | 5/1993 | Kitaevich et al |
| 5,151,192 | 9/1992 | Matkovich et al |
| 5,150,705 | 9/1992 | Stinson |

Other Publications

Barger, G. and E. K. Knott. 1950. "Blood: Ultraviolet Irradiation (Knott Technique)", Medical Physics 11: 132–6.

Miley, G. P., R. C. Olney, and H. T. Lewis. 1997. "Ultraviolet Blood Irradiation: A History and Guide to Clinical Application (1933–1997)", Silver Spring, Md.: Foundation for Blood Irradiation.

Schleicher, C. 1995. "Application of Ultraviolet Blood Irradiation for Treatment of HIV and Other Bloodborne Viruses." Townsend Letter for Doctors and Patients, 147:66–72.

Lee, P. A., G. W. Weger, R. W. Pryor, and J. R. Matson. 1998. "Effects of Filter Pore Size on Efficacy of Continuous Arteriovenous Hemofiltration Therapy for Staphylococcus Aureus-induced Septicemia in Immature Swine". Crit. Care Med. 26(4):730–37.

Sibbald, W. J. and J.-L. Vincent (Eds.) 1995. "Clinical Trials for the Treatment of Sepsis", Springer-Verlag, Berlin, Heidelberg.

SUMMARY OF THE INVENTION

A method and apparatus for preventing and treating septicemia is described. The extracorporeal system includes an anti-microbial device to kill at least 99% of bloodborne microorganisms, a hemoconcentrator/filtration unit to remove approximately 90% of the bloodborne target molecules from patient's blood and a filter unit to remove the same target molecules from the ultra-filtrate. Target molecules are produced by microorganisms, as well as the patient's cells, and include endotoxins from gram negative bacteria, exotoxins from gram positive and gram negative bacterial and mediators such as RAP protein from *Staphylococcus aureus,* and cell mediators such as tumor necrosis factor-alpha, and interleukin 1-beta, complement proteins C3a and C5a and bradykinin.

The present invention is a method and apparatus for the continuous processing of diluted blood by a venovenous route using a double lumen cannula and a filter having a pore size of 60–95 kD. The system will remove substances, including target molecules, comparable to Lee et al.

The present invention also can filter the plasma filtrate for subsequent return of important smaller molecules to the patient.

Since hemodilution has already occurred during cardiopulmonary bypass, the filter will function in an extracorporeal circuit to remove inflammatory mediators caused by the cardiopulmonary bypass. Currently, special bonded circuits as well as pharmaceutical products are used to reduce the effects described during extracorpreal circulation.

DESCRIPTION OF PREFERRED EMBODIMENTS

Figure 1:
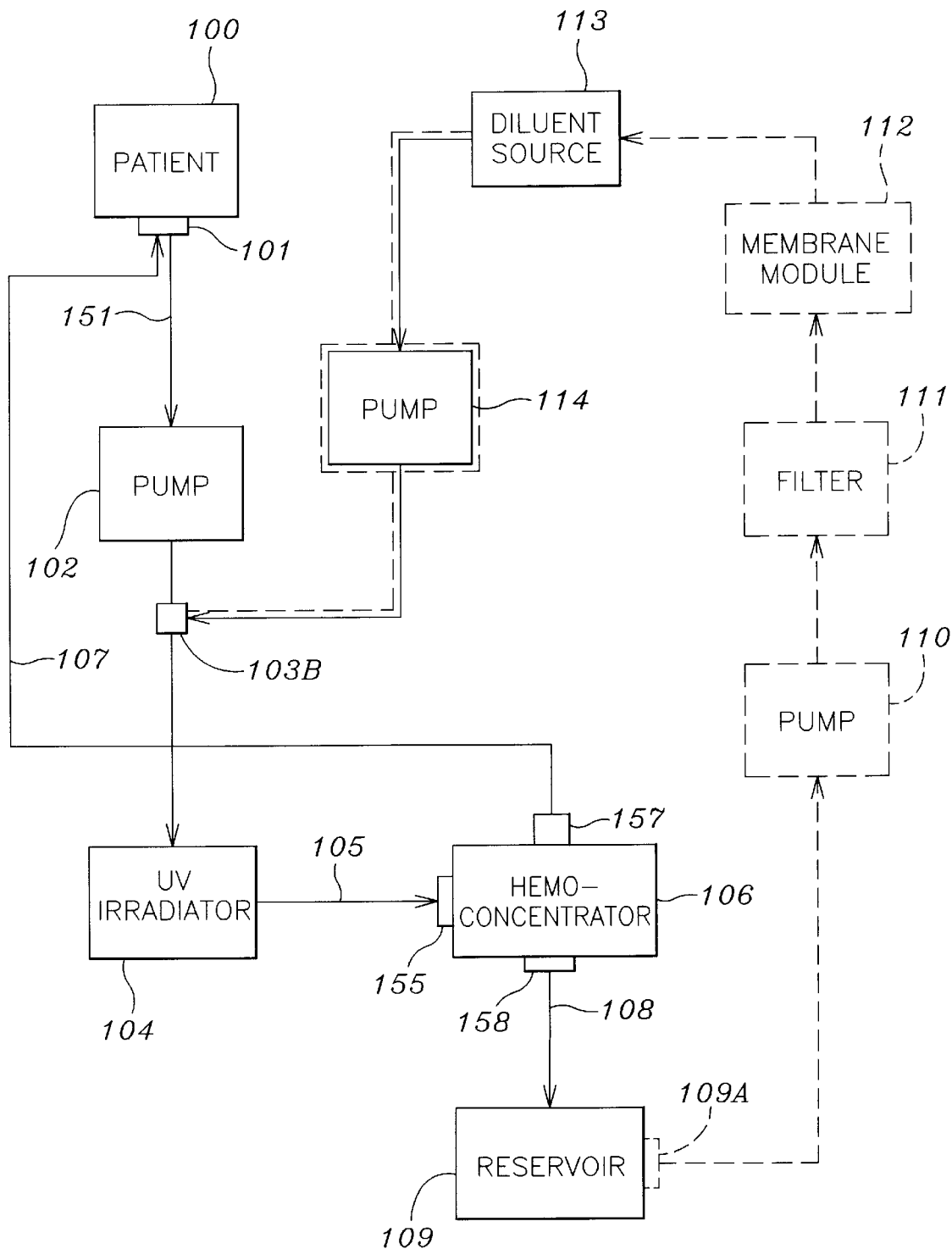
FIG. 1 is a schematic representation of one embodiment of the system of the instant invention, i.e. direct application to a patient not undergoing extracorporeal circulation.

Referring now to FIG. 1, there is shown a schematic representation of the system of the instant invention, including several alternative configurations. The septicemia prevention and treatment system (SPATS) comprises a plurality of components, typically, connected by standard medical extracorporeal tubing and connectors. As such, the system may be attached to a patient via cannulation or it may be incorporated into extracorporeal circuitry already serving a patient such as in hemodialysis or cardiopulmonary bypass (see, for example, FIG. 2) or hemodialysis. As represented herein, the SPATS component circuitry most resembles that of modern hemodialysis in terms of vascular access, bypass mode (venovenous or arteriovenous), blood flow rate, the use of a hemoconcentrator (a device constructed in the fashion of a dialyzer), and duration of application. Therefore, some or all of the components described herein could be incorporated into a hemodialysis system, as well.

As noted, FIG. 1 shows one embodiment of the system of the instant invention, including several alternative configurations. As in hemodialysis, blood from the patient 100 enters the SPATS tubing 151 via a suitable connector such as a venous cannula 101 of sufficient diameter to permit drainage flow of whole blood up to about 300 ml/min. Double lumen cannulae that satisfy this requirement are available and, thus, permit return flow as well, for example, via. tubing 107, as described hereinafter. This latter technique is not required, but has the advantage of reducing vascular access to a single site such as, but not limited to, a brachial vein.

The patient's venous blood proceeds via polyvinyl chloride (PVC) or other suitable tubing to a pump 102, which can be a positive displacement or centrifugal pump, for example, which regulates flow at about 200–300 ml/min. through the system.

As shown in FIG. 1, blood from pump 102 passes through a polycarbonate "Y" connector 103B where the blood mixes with a suitable isotonic diluent, such as plasmalyte solution. A variety of such solutions, referred to as "crystalloids", are available. The diluent is supplied from diluent source 113 which, typically, comprises a large capacity reservoir for storing an admixture of reclaimed (or converted) ultrafiltrate.

The diluent is delivered by pump 114 which can be a roller pump or the like at a flow rate which results in a hematocrit of about 10–20%.

Figure 3:
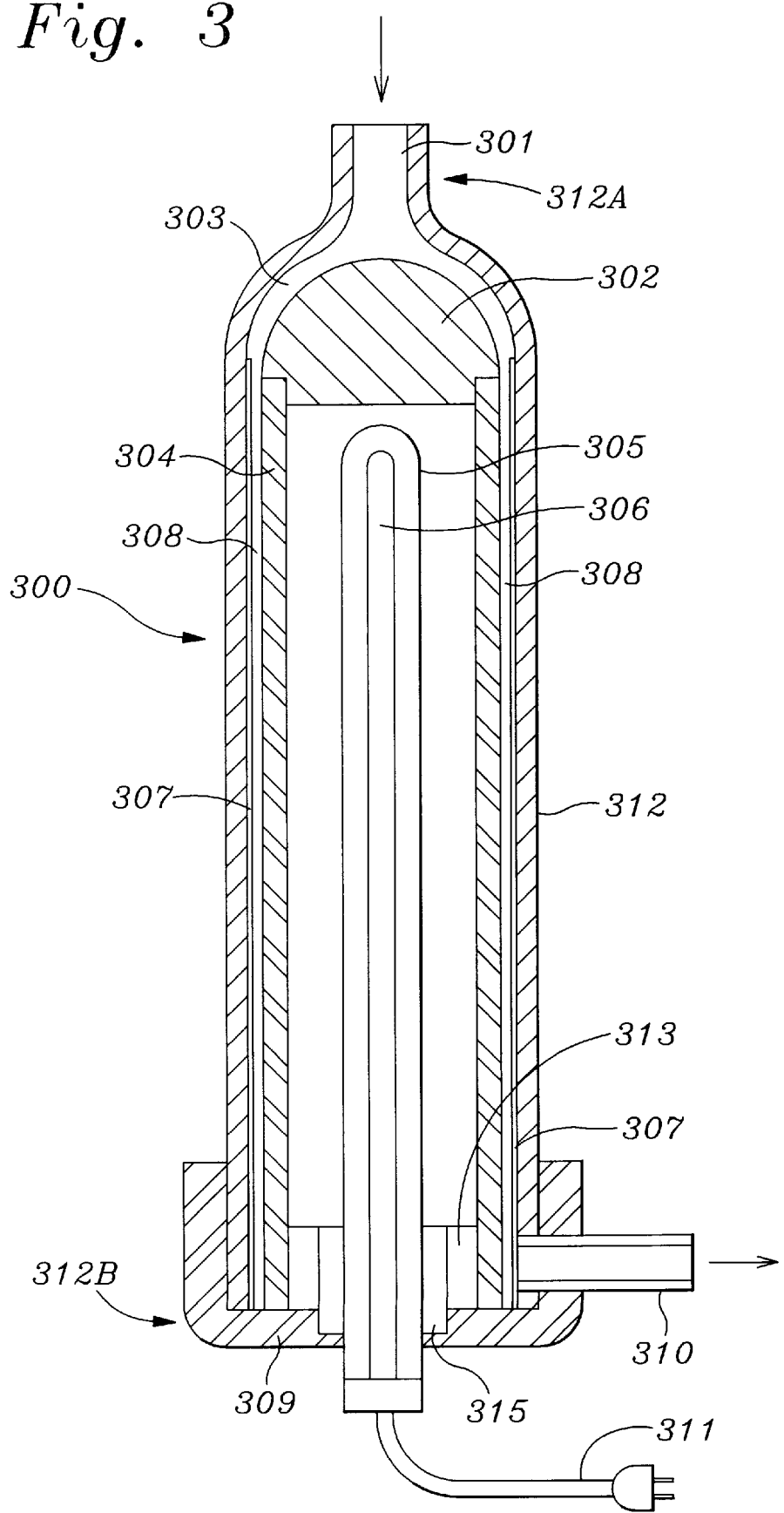
FIG. 3 is a cross-sectional view of one embodiment of an ultra-violet irradiator used in the instant invention.
Figure 4:
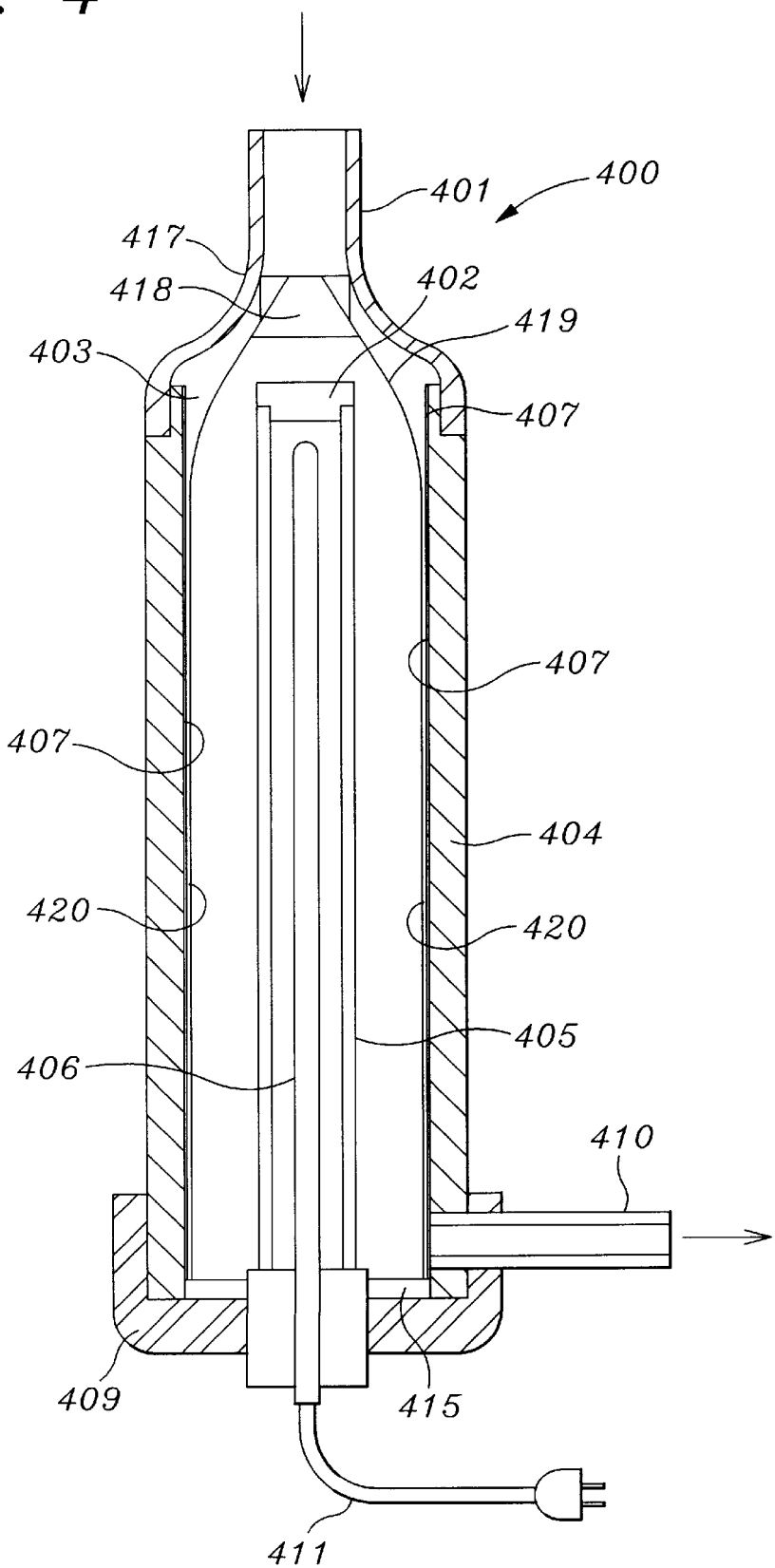
FIG. 4 is a cross-sectional view of another embodiment of an ultra-violet irradiator used in the instant invention using a filming technique.

The diluted venous blood then passes through tubing to the bactericidal ultraviolet (UV) irradiation device 104 (shown schematically in FIGS. 3 and 4). Controlled in-vitro experiments have demonstrated that UV irradiation is substantially more effective as a bactericidal agent when whole blood (35–45% hematocrit) is diluted to a hematocrit of about 10–20% (see Table II). Furthermore, when diluted blood is presented to the hemoconcentrator 106, target molecules are more effectively removed by sieving, as described infra.

| Period of Treatment (minutes) | 60 | 90 | 120 |
|---|---|---|---|
| HEMATOCRIT % | | | |
| 0 | 99.75 | 99.97 | 99.99 |
| 20 | 97.26 | 99.44 | 99.98 |
| 38 | — | 82 | 86.2 |
| Whole Blood | — | 49.4 | 66.9 |
| | Percent Reduction | | |

The above data represents testing performed with varying flow rates and various anticoagulants and prototype UV delivery systems in four (4) liters of animal blood treated with UVC at room temperature. The four (4) liter volume represents a mammal, including human, of approximately 123 pounds.

The diluted blood leaves the UV device 104 and passes through tubing 105 and connector 155 to a hemoconcentrator 106 which has approximately 1.2 to 2.4 m² exchange surface with pore size of about 60–95 kD. The hemoconcentrator 106 (described relative to FIG. 6) is preferably oriented vertically in the SPATS so that blood flows from bottom to top. This arrangement aids in priming and debubbling the SPATS with crystalloid diluent before blood enters the circuit. In actual practice, positioning the hemoconcentrator 106 a few centimeters below the patient but as far above the floor of the treatment area as practicable provides the potential for maximal ultrafiltration flow by gravity drainage.

The blood leaves the hemoconcentrator 106 at port 157 at a hematocrit approximating its entry into the SPATS and returns to the patient via tubing 107 and double lumen cannula 101.

The pressure across the hemoconcentrator 106 is monitored at sample ports and decreases about 70–100 mmHg from inlet 155 port to outlet 157 port at a combined blood and diluent flow of 400–500 ml/min and blood hematocrit of about 20%. At a constant flow rate, a decrease in hematocrit results in a lesser pressure drop and lower inlet pressure, while an increase in hematocrit results in a greater pressure drop and higher inlet pressure. Thus, changes in inlet pressure signal changes in hematocrit and on-line monitoring of pressure can aid a technician in regulating hematocrit. Additionally, hematocrit can be monitored by an in-line optical device or the like, if so desired.

The material filtered from the blood is collected in a filtrate collection reservoir 109 via tubing 108 connected to the outlet port 158. The reservoir 109 is designed to be disposable in a preferred embodiment.

Among other factors, the ultrafiltrate rate is dependent on membrane area, relative amount of diluent flow, i.e., hematocrit, and transmembrane pressure (TMP). In this system, the volume of ultrafiltrate realized is maximized if the collection reservoir 109 is placed a substantial distance below the hemoconcentrator 106 in the operating arena. Typically, this distance is about two feet. This configuration increases the TMP because the increased negative (siphon) pressure results in increased untrafiltration rate. Ultrafiltrate collected from the hemoconcentrator 106 can be discarded (in an approved manner) or conserved within the SPATS.

In an alternative system configuration, pump 110 (such as a roller pump or the like) propels the ultrafiltrate from reservoir 109 through a secondary circuit (shown in dashed lines). The secondary circuit or path operates independently of the primary circuit and includes filter 111 which is, typically, constructed of several layers of positively-charged meltblown fabric. The filter 111 is designed for the removal of endotoxins containing protein and negatively charged lipopolysaccharide (LPS). That is, the filter fabric captures 94% of endotoxin LPS which is liberated from the cell wall of disrupted gram negative bacteria. In a preferred embodiment, the fabric is produced in a five-layer configuration.

Other target molecules mainly pass through filter 111 and are removed by a hollow fiber membrane module 112 with a porosity of about 10 kD, for example. Endotoxin, from the cell wall of Gram negative bacteria and containing protein and negatively-charged lipopolysaccharide (LPS), is 99% captured in filter 111. Thus, the majority of the smaller molecules pass through filter 111 and module 112 to the large-capacity diluent reservoir 113 where they mix with crystalloid. Pump 114 propels the admixture of crystalloid and filtrate from the secondary circuit back to the primary circuit via Y-connector 103. Thus, smaller molecules can be conserved by passage thereof completely through the secondary circuit, while plasma proteins and other large molecules are conserved by retention thereof in the primary circuit at the hemoconcentrator.

Pump flow is initially based on the hematocrit of the patient 100 and can be subsequently regulated with knowledge of hemoconcentrator inlet pressure as determined by inlet port 155. That is, port 155 may include a stopcock for monitoring the inlet pressure and/or for sampling of the fluid. Connection of the components in the secondary circuit is by tubing. Components 111 and 112 may be physically incorporated into diluent reservoir 113, thereby eliminating some connecting tubing and, thereby simplifying supplying the circuit.

An on-line optical sensor for the purpose of monitoring hematocrit during hemodialysis has been reported by Jabara and Murta (1995). In this arrangement, electrical feedback control from such a sensor to pump 114 would eliminate the need for manual control at this point of the system.

In one embodiment, a single pump 102, positioned as shown, regulates patient blood and diluent flows. Either a pump with the capability of dual raceway control or a traditional single raceway pump coupled with thumb screw control of diluent flow can be used. In the latter case, the pump flow would be regulated at 400–500 ml/min, accounting for the combined flows from the patient 100 and the diluent reservoir 113.

In the first embodiment, the secondary circuit, shown in dashed outline, is eliminated and the ultrafiltrate from the hemoconcentrator 106 is collected in reservoir 109 and discarded. The diluent source 113 remains, however. This version is likely to be deployed in the case where supplementing important small molecules is more cost effective than conserving them.

The rate of pump 110 can be regulated via feedback from a negative pressure controller 109A established on the reservoir 109. This eliminates the need for human operation of pump 110.

Figure 2:
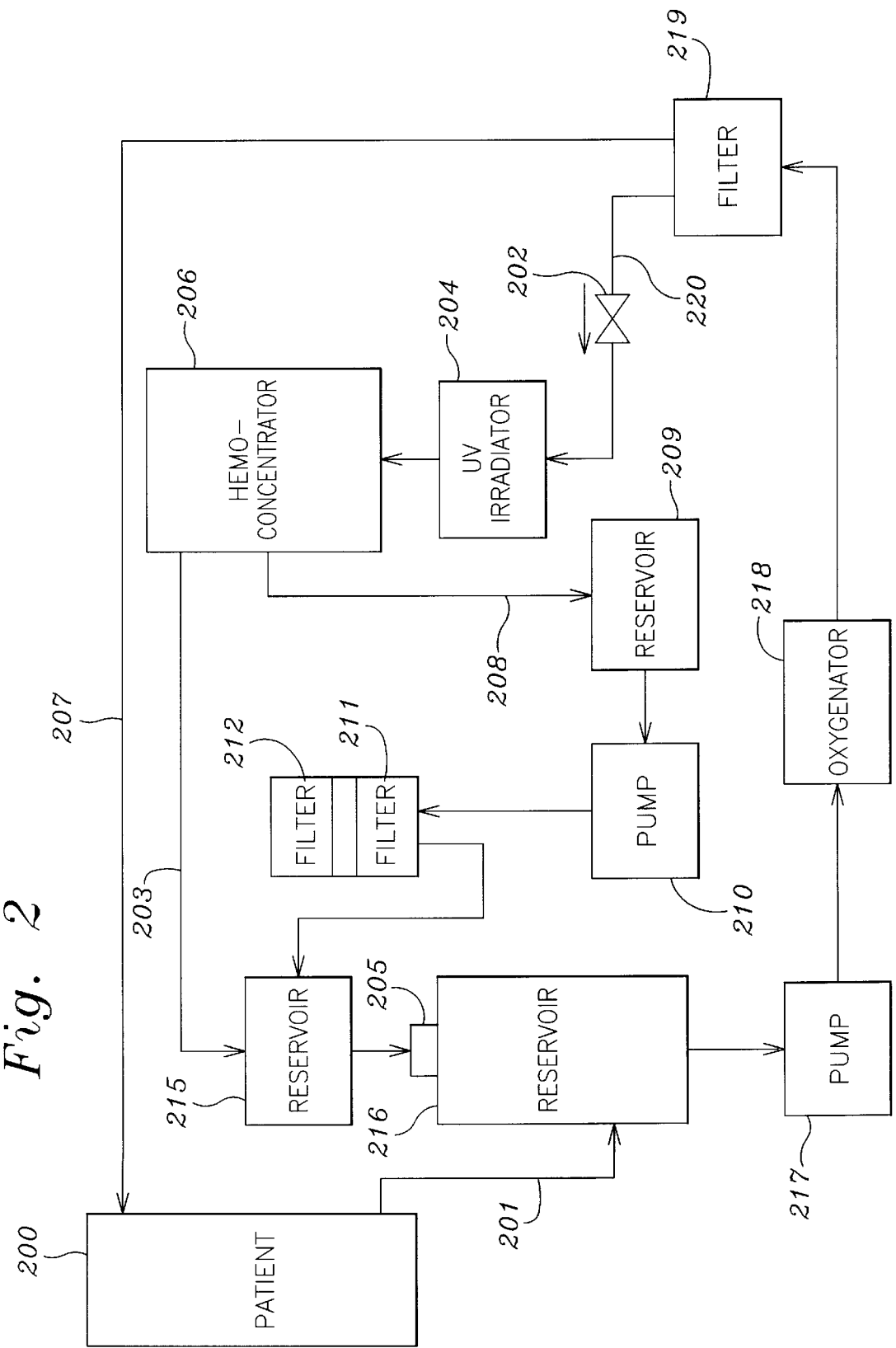
FIG. 2 is a schematic representation of another embodiment of the system of the instant invention, i.e. its application within an extracorporeal circuit already serving as cardiopulmonary support for a patient.

In FIG. 2, the SPATS is shown in a cardiopulmonary bypass (i.e. open heart blood oxygenator) circuit. In this embodiment, the blood of the patient has already been diluted to a hematocrit of 20–25%. Thus, blood from the patient 200 drains via connecting tubing 201 to a venous reservoir 216 from which pump 217 supplies the blood to a membrane oxygenator 218 where it is arterialized (i.e. oxygenated). The oxygenated blood is passed through an arterial filter 219 from which most of the arterialized blood is returned to the patient via tubing 207.

However, arterialized blood which is to be processed by the SPATS is shunted via purge line 220 from the arterial filter 219 to the cardiotomy reservoir 215 via a one-way valve 202. The shunt flow range is 300–400 ml/min under the usual total CPB total flow of 4–6 liters per minute.

Ultrafiltrate may be pumped and regulated with a negative pressure feedback controller through the target molecule removal system including UV source 204 and hemoconcentrator 206 into the same cardiotomy reservoir 215 via connecting tubing 203 and another inlet. Blood and/or ultrafiltrate collecting in the reservoir 215 is conveyed to the venous reservoir 216 at inlet 205 completing the cardiopulmonary bypass circuit (CPB).

As an alternative, 20–25% hematocrit blood could be diluted to 10–15% hematocrit using diluent available to CPB bypass in the fashion described previously. The ultrafiltrate is collected in reservoir 209 connecting tubing 208 from which it is pumped through filters 211 and 212 by pump 210 for removal of target molecules. This operation makes the bactericidal effects of UV device 204 and the sieving of target molecules through the hemoconcentrator 206 even more effective. This approach has the benefit of potentially shortening the duration of treatment. In either case, blood passes through the primary SPATS circuit, consisting of UV irradiator 204 and hemoconcentrator 206.

Ultrafiltration occurs in the hemoconcentrator 206 at the pressure drop previously indicated much as it does in the glomerular units of the natural kidney. However, the natural kidney prevents the passage of the small and plentiful plasma protein albumin (67–69 kD molecular weight) and permits occasional passage of free plasma hemoglobin (64 kD molecular weight), thereby demonstrating a sharp cutoff at a molecular weight of about 65 kD. The hemoconcentrator 206, with 60–95 kD porosity, is relatively effective at prohibiting passage of plasma proteins (<5% of plasma albumin, <2% of plasma globulin sieved) while permitting sufficient passage of electrolytes, BUN, and glucose to insure normal plasma osmolality. Larger molecules such as cholesterol and creatinine are incompletely sieved (25–95% of plasma concentrations). Permeability of target molecules TNF, IL-1B and LPS are about 100% (appearing in the ultrafiltrate in concentrations equivalent to plasma) in this system; IL-2, although about the same molecular weight as IL-1B (i.e. 17 kD), is almost entirely retained in the blood (primary circuit), thereby reminding that factors other than simple molecular weight are important. Thus TNFa, IL-1β, and LPS have a high percentage potential for removal by this system.

Referring now to FIG. 3, there is shown a cross-sectional view of one embodiment of a UV irradiator 300 used in the instant invention. The irradiator 300 includes an outer cylinder 312 which is, typically, molded or otherwise formed of polycarbonate or similar material. The cylinder 312 is, typically, open at end 312A and substantially closed at end 312B with a small inlet 301 therethrough. In one embodiment, the cylinder 312 (including the inlet 301) is approximately 18 to 20 inches long and about 1 inch inside diameter. The inlet 301 is about 3/16 inch inside diameter and about ½ inch long or any suitable length for secure connection to the tubing described supra.

The irradiator 300 includes a conventional ultra-violet light source 306 with a radiation wavelength of 254 nm although other suitable sources can be utilized. The UV source 306 is connected to a suitable power source via connector 311. The UV source 306 is enclosed within a quartz tube 305 which is doped with cesium or any other suitable material which blocks ozone producing wavelengths.

The UV assembly, including quartz tube 305, is mounted within hollow, open-ended quartz tube 304 which is transparent to UV light. As will be seen, the tube 304 protects the UV light source 306 and the protective tube 305 therefore. The tube 304 is a part of the disposable portion of the irradiator 300.

Top cap 302, fabricated of polycarbonate is sealed tightly to the upper end of quartz tube 304 and establishes a chamber 303 between the top cap 302 and the inner surface of the upper end of cylinder 312. An annular bushing 313 surrounds quartz tube 305 and securely positions the UV assembly (source 106 and tube 305) within tube 304. Seal 315, formed of silicone for example, tightly seals the bushing 313 in the doped quartz tube 304 adjacent the open bottom thereof and positions the lower end of UV source 306 therein.

Bottom end cap 309, fabricated of polycarbonate, is attached to the outer surface of cylinder 312, for example, by ultrasonic welding, adhesive or the like. An outlet 310, typically of about ¼ inch diameter and of suitable length to provide a secure connection to tubing as described supra, extends outwardly from tube 312 and bottom cap 309.

In a preferred embodiment, the outer surface of cylinder 304 and the inner surface of cylinder 312 are spaced apart by an annular passageway 308 of about 0.006–0.015 inches in order to establish a narrow space for blood flow therethrough. Likewise, at least one of these surfaces is coated with a thin layer 307 of hydrophilic material such as parylene and then plasma treated in order to produce a surface contact angle of less than 5° whereby the fluid passing through the passageway 308 will flow readily as a sheet or film.

In operation, heparinized blood in the extracorporeal circuit shown in FIGS. 1 or 2 enters the inlet 301 and then into chamber 303 at the upper end of tube 312. The chamber 303 is kept as small as possible with a typical volume of less than 20 cc. The blood flows around top cap 302 which has, preferably, a rounded upper surface, and into the annular passageway 308. The blood flows downward in this passageway. The flow is maximized by the hydrophilic coating 307 with a contact angle of 0°–5° which keeps the surface tension to a minimum, thus reducing the possibility of stagnant areas that can cause fibrin to deposit and, eventually, cause clots to form. A heparin-bonded surface is also an option to preventing thrombus formation or possibly combining bonded heparin and hydrophilic treatment. The blood continues down the annular passageway 308 and pools at the bottom of the bottom cap 309. The blood is then routed out of the irradiator 300 through outlet 310.

Inasmuch as the UV assembly is sealed from the blood flow by bushing 313 and seal 315 as noted, the UV assembly—including UV source 306—is reusable while the other components including tube 304 are disposable.

Referring now to FIG. 4, there is shown a cross-sectional view of another embodiment of a an irradiator, viz. UV irradiator 400, used in the instant invention. Once again, as in FIG. 3, a UV lamp 406, approximately 18" long, radiates at about 254 nm radially through a doped quartz jacket 405 to prevent ozone producing UV wavelengths. The UV rays emanate through a ½" to 1" diameter quartz jacket or tube 405 which is transparent to UVC (i.e. type C UV radiators) and which is closed at the top end with a cap 402, preferably formed of polycarbonate, and then sealed and adhered to the bottom of tube 405 with silicone adhesive 415. The silicone adhesive prevents and cracking of quartz tube 405 with changes of temperature during operation. An electrical cord 411 connects to an external power source.

In this embodiment, the outer tube 404 is a cylinder which is closed by a top cap 417 bonded with an adhesive or ultrasonically welded to a diverter 418 formed therewith.

In addition, an approximately 0.01 inch thick cone-shaped wiper 419, made of polyester or polycarbonate, is formed in cylinder 404. The wiper distends slightly under pressure from blood flow allowing a thin, uniform film 420 of blood to flow past the wiper onto the inner surface of the cylinder 404.

In operation, blood enters inlet 401 which is integral with top cap 417 and flows around diverter 418. The diverter 418 also disperses the blood evenly through a small chamber 403 formed by diverter 418 and top cap 417, which is, typically, less than 20 cc. The blood in chamber 403 flows onto cone shaped wiper 419 which is flexible and will distend slightly under pressure from an external pump (not shown). The wiper 419, thus, causes a film 420 of blood to emanate circumferencially, and downwardly, along the inside wall of cylinder 404 and, finally, into a small pool of blood in bottom cap 409. The blood then exits through outlet port 410 under pressure from an external pump in the system as described supra.

As previously noted, the blood film is sufficiently diluted with saline (10 to 20% hematocrit) and thin enough (approximately 0.006 to 0.020 thick) to allow the UVC light radiation (i.e. UV light radiation of range C) from source 406 to penetrate easily. The hydrophilic coating 407 or treatment reduces the contact angle of the base plastic of the cylinder to 0° to 5° allowing the blood to film uniformly and inhibit dribbling downward.

The significance of a filmer approach, as shown in FIG. 4, is that the outermost portion of the blood film 420 is moving faster than the boundary layer thereby exposing more blood to the UV light although it may be more difficult to control the blood flow.

Figure 5:
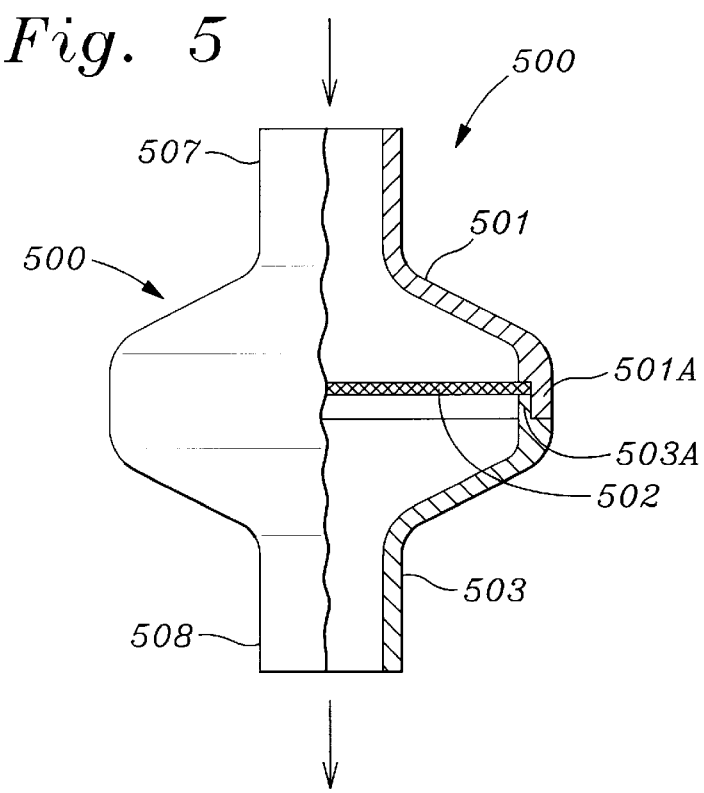
FIG. 5 is a partial cross-sectional view of one embodiment of a filter used in the instant invention to remove target molecules from untrafiltrate.

Referring now to FIG. 5, there is shown a partially broken away, partially cross-sectional view of a filter 500. The unit 500 includes a top cap 501 and a bottom cap 503 with an inlet 507 and an outlet 508, respectively. The top and bottom caps are, typically, cone shaped with generally circular configurations. The caps include mating edges 501A and 503A, respectively. The edges can be reversed from those shown in FIG. 5 or take any alternative shape, so long as a secure seal between the caps can be achieved.

Mounted within the unit 500, typically, secured by the mating edges 501A and 503A, is a filter 502. In this embodiment, the filter is fabricated of an electrostatically charged, melt blown, layer of polypropylene with a minimum basis weight of 140 grams/square meter. In a preferred embodiment, the filter comprises seven (7) layers each of which is 20 grams/square meter although this number of layers is not intended to be limitative. The filter area should be sufficiently large to handle the filtrate flow rate. Ideally, a filter with a minimum area of 27 square inches is selected.

In operation, filtrate flows into top cap 501 through inlet 507 and onto and through the charged, meltblown polypropylene filter 502. The endotoxins are removed from the blood by electrostatic attraction in filter 502. Since the blood proteins such as albumin, have been retained by a hemoconcentrator (e.g. hemoconcentrator 206) they do not foul the filter media and fight for sites on the media fibers.

Figure 6:
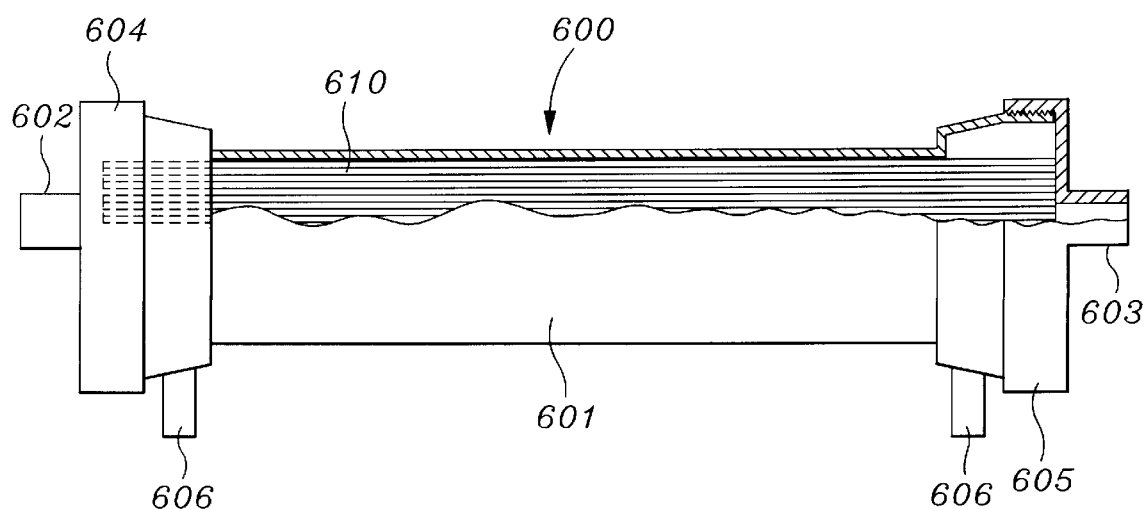
FIG. 6 is a partially broken away elevation view of a hemoconcentrator used in the instant invention.

Referring now to FIG. 6, there is shown a partially broken away elevation view of a hemoconcentrator 600 which corresponds to the hemoconcentrator 106 or 206 described supra. The hemoconcentrator is constructed of a hollow cylinder 601 formed of polycarbonate or similar material. The cylinder is, in one embodiment, approximately 10" long and 1.5" in diameter. An inlet 602 and an outlet 603 of suitable configuration to be attached to conventional medical tubing are provided in caps 604 and 605 at opposite ends of the cylinder. The caps are, typically, threadedly attached to the cylinder. In addition, at least one effluent or drainage port 606 is provided adjacent one end of the cylinder. The interior of the cylinder is filled with filter material 610 comprising polysulphone hollow fibers, has between 1.2 and 2.4 m² area with a nominal pore size of 60,000 to 95,000 Daltons capable of removing blood proteins and cell mediators whose molecular weight is less than 55,000 Daltons. Because the blood is diluted to 10% to 20% hematocrit, the gel layer formed by the blood, is not thick enough to substantially reduce the effective pore size of the hollow fibers. It is estimated that the pore size is reduced 5% to 20% by the gel layer formed by the layer.

A hollow fiber or filter surface area of about 1.2 to 2.4 m² is desirable to provide sufficient area to reconstitute the diluted blood in volumes equivalent to those added to the circuit. This is significant because blood returning to a septic patient must not be substantially diluted because that patient will, typically, have secondary pulmonary dysfunction.

Thus, there is shown and described a unique design and concept of a septicemia prevention and treatment system. The device described in this patent is capable of preventing and/or treating SIRS by any etiology although the emphasis is on septicemia or microbial sepsis. The particular configuration shown and described herein relates to a Septicemia Prevention and Treatment System. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

What is claimed is:

1. A blood treatment system including,
a UV irradiation device connected to receive and irradiate blood containing biological toxins from a source of blood,
a diluent source for supplying a diluent to the blood to be received by said UV irradiation device in order to significantly reduce the hematocrit of the blood,
a concentrator device to receive blood from said UV irradiation device in order to filter the blood and to remove the diluent therefrom,
a return path connected for returning filtered blood from said concentrator device to the source of blood, and
a recycle path connected for returning the diluent removed from the blood by said concentrator device to said diluent source.

2. The system recited in claim 1 wherein,
said recycle path includes a filter.

3. The system recited in claim 2, wherein,
said filter in said recycle path includes an electrostatically charged, melt-blown material.

4. The system recited in claim 1 including,
a filter device connected to receive blood from the source and to supply a portion of the received blood to said UV irradiation device and to return the remainder of the received blood to the source.

5. The system recited in claim 4 including,
an oxygenator connected between the source and said filter device in order to oxygenate the blood received from the source.

6. The system recited in claim 1 including,
at least one pump connected to said system for moving said blood through the system.

7. The system recited in claim 1 wherein,
said irradiator device comprises,
a UV light source, and
a fluid chamber adjacent to said UV light source,
said fluid chamber confining said fluid to a thin film for exposure to said UV light source.

8. The system recited in claim 1 wherein,
said concentrator comprises, a hollow cylinder, and
a central core formed of hollow fibers axially disposed within said hollow cylinder.

9. The system recited in claim 1 wherein,
said return path includes tubing.

10. The system recited in claim 1 wherein,
said return path includes a double lumen cannula.

11. The system recited in claim 1 including,
a reservoir connected to receive material filtered from the blood by said concentrator device.

12. The system recited in claim 1 wherein,
said recycle path includes a membrane module.

13. The system recited in claim 1 wherein,
said recycle path includes a recycle pump.

14. The system recited in claim 1 including,
inlet monitoring means at said concentrator device for monitoring the pressure of the blood received thereby from said UV irradiation device.

15. The system recited in claim 1 wherein,
said concentrator device filters the blood received thereby by the size of the constituents of the blood.

16. The system recited in claim 1 wherein,
said diluent source supplies a diluent which reduces the blood to a hematocrit of about 10% to 20%.

17. A system for removing toxins from the blood of a patient comprising,
removal means for removing blood from the patient,
dilution means for supplying a diluent to the blood for diluting the blood which has been removed from the patient,
irradiation means for irradiating the diluted blood in order to inactivate the toxins in the diluted blood,
extraction means for extracting cell mediators and diluent from the blood after inactivation by said means for irradiation,
return means for returning the blood from the extraction means to the patient after the cell mediators and diluent have been extracted therefrom, and
a recycle path including a filter device for passing said diluent from said extraction means to said dilution means.

18. The system recited in claim 17 wherein,
said irradiator means comprises,
a UV light source, and
a fluid chamber adjacent to said UV light source,
said fluid chamber confining said fluid to a thin film for exposure to said UV light source.

19. The system recited in claim 17 wherein,
said extraction means comprises,
a hollow cylinder, and
a central core formed of hollow fibers axially disposed within said hollow cylinder.

20. The system recited in claim 17 wherein,
said return means includes tubing.

21. The system recited in claim 17 wherein,
said return means includes a double lumen cannula.

22. The system recited in claim 17 including,
a reservoir connected to said extraction means in order to receive material extracted from the blood by said extraction means.

23. The system recited in claim 17 wherein,
said recycle path includes a recycle pump.

24. The system recited in claim 17 including,
inlet monitoring means for monitoring the pressure of the blood received at the input of said extraction means.

25. The system recited in claim 17 including,
a filter device connected to receive blood from the source and to supply a portion of the blood to the irradiation means and to return the remainder of the received blood to the source.

26. The system recited in claim 17 including,
an oxygenator connected between the source and said filter device in order to oxygenate the blood received from the source.

27. The system recited in claim 17 wherein,
said dilution means supplies a diluent which comprises a crystalloid.

28. The system recited in claim 17 including,
a pump device for pumping blood through said system.

29. A system for removing toxins from the blood of a patient comprising,
apparatus for removing blood from the patient,
a diluent source for supplying a diluent to the blood which has been removed from the patient for the purpose of diluting the blood and reducing the hematocrit thereof,
first filter means having a porosity of about 60–95 kilodaltons for receiving the blood and extracting cell mediators and diluent therefrom,
second filter means having a porosity of about 10 kilodaltons for receiving the output from said first filter means including cell mediators and diluent and extracting the cell mediators therefrom,
first means for returning a portion of the blood to the patient after the cell mediators and diluent have been extracted therefrom by said first filter means, and
second means for returning the diluent to said diluent source after the cell mediators having been extracted therefrom by said second filter means.

30. The system recited in claim 29 wherein,
said first filter means includes filter material comprising hollow polysulphone fibers.

* * * * *